(12) United States Patent
Oakley et al.

(10) Patent No.: US 7,838,464 B2
(45) Date of Patent: Nov. 23, 2010

(54) METHOD FOR YIELD IMPROVEMENT IN GLYPHOSATE-RESISTENT LEGUMES

(75) Inventors: Peter Oakley, Neustadt (DE); Annette Freund, Limburgerhof (DE); Klaus Scheiberger, Gönnheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 537 days.

(21) Appl. No.: 10/534,637

(22) PCT Filed: Nov. 8, 2003

(86) PCT No.: PCT/EP03/12483

§ 371 (c)(1),
(2), (4) Date: May 12, 2005

(87) PCT Pub. No.: WO2004/043150

PCT Pub. Date: May 27, 2004

(65) Prior Publication Data

US 2006/0111239 A1 May 25, 2006

(30) Foreign Application Priority Data

Nov. 12, 2002 (DE) ................ 102 52 881

(51) Int. Cl.
  *A01N 63/00* (2006.01)
  *A01N 43/653* (2006.01)
  *A01N 57/18* (2006.01)
  *A01N 57/08* (2006.01)
  *A01N 43/64* (2006.01)

(52) U.S. Cl. .................. 504/118; 504/128; 504/206; 504/272; 514/129; 514/357; 514/359; 514/406

(58) Field of Classification Search ............. 504/128, 504/272, 282, 118, 206, 275; 514/357, 359, 514/406
See application file for complete search history.

(56) References Cited

U.S. PATENT DOCUMENTS

| | | | |
|---|---|---|---|
| 3,988,142 A | 10/1976 | Franz | |
| 3,991,071 A | 11/1976 | Brookes et al. | |
| 4,652,580 A | 3/1987 | Janssen et al. | |
| 4,723,984 A | 2/1988 | Holmwood et al. | |
| 4,829,085 A | 5/1989 | Wenderoth et al. | |
| 4,937,372 A | 6/1990 | Wenderoth et al. | |
| 5,157,037 A | 10/1992 | Schuetz et al. | |
| 5,194,662 A | 3/1993 | Brand et al. | |
| 5,395,854 A | 3/1995 | Brand et al. | |
| 5,534,550 A | 7/1996 | Gerdes et al. | |
| 5,789,430 A | 8/1998 | Jautelat et al. | |
| 5,824,705 A | 10/1998 | Mueller et al. | |
| 5,869,517 A | 2/1999 | Muller et al. | |
| 5,874,467 A | 2/1999 | Bayer et al. | |
| 5,935,965 A | 8/1999 | Kirstgen et al. | |
| 5,948,932 A | 9/1999 | Grote et al. | |
| 5,981,581 A | 11/1999 | Bayer et al. | |
| 6,225,349 B1 | 5/2001 | Bayer et al. | |
| 6,235,743 B1 | 5/2001 | Bayer et al. | |
| 6,355,634 B1 | 3/2002 | Isenring et al. | |
| 6,482,984 B2 | 11/2002 | Grammenos et al. | |
| 2003/0060371 A1* | 3/2003 | Asrar et al. | 504/272 |

FOREIGN PATENT DOCUMENTS

| | | |
|---|---|---|
| EP | 0 178 826 A2 | 4/1986 |
| EP | 0 196 038 A2 | 10/1986 |
| EP | 0 253 213 A1 | 1/1988 |
| EP | 0 254 426 A2 | 1/1988 |
| EP | 0 278 595 A2 | 8/1988 |
| EP | 0 280 185 A2 | 8/1988 |
| EP | 0 350 691 A2 | 1/1990 |
| EP | 0 370 629 A1 | 5/1990 |
| EP | 0 382 375 A2 | 8/1990 |
| EP | 0 398 692 A2 | 11/1990 |
| EP | 0 398 692 B1 | 11/1990 |
| EP | 0 460 575 A1 | 12/1991 |
| EP | 0 463 488 A1 | 1/1992 |
| EP | 0 477 631 A1 | 4/1992 |
| EP | 0 628 540 A1 | 12/1994 |
| EP | 0 808 569 A | 11/1997 |
| EP | 1 118 609 A2 | 7/2001 |
| GB | 1 522 657 A | 8/1978 |
| GB | 2 253 624 A | 9/1992 |
| WO | WO-92/13830 A1 | 8/1992 |
| WO | WO-95/18789 A1 | 7/1995 |

(Continued)

OTHER PUBLICATIONS

Ramsdale et al., Res. Rep. North Cent. Weed. Sci. Soc., vol. 59, 2002, pp. 280-283.

(Continued)

*Primary Examiner*—Mina Haghighatian
*Assistant Examiner*—Andriae M Holt
(74) *Attorney, Agent, or Firm*—Birch, Stewart, Kolasch & Birch, LLP

(57) ABSTRACT

Method for increasing the yield in glyphosate-resistant legumes, which comprises treating the plants or the seed with a mixture comprising
  a) a compound of the formula I

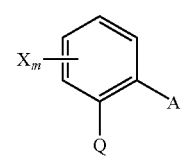

where
  X, m, Q, A have the meaning given in the description and
  b) a glyphosate derivative II
in a synergistically active amount.

11 Claims, No Drawings

FOREIGN PATENT DOCUMENTS

| | | |
|---|---|---|
| WO | WO-95/24396 A1 | 9/1995 |
| WO | WO-96/01256 A1 | 1/1996 |
| WO | WO-96/16047 A1 | 5/1996 |
| WO | WO-97/36488 A1 | 10/1997 |
| WO | WO-99/45781 A | 9/1999 |

OTHER PUBLICATIONS

Derwent Abstract: DW-97-110074/11, 1997.
Derwent Abstract: DW-97-145582/13, 1997.
Derwent Abstract: DW-1999-419076/35, 1999.
Glaab et al., *Planta*, vol. 207, 1999, pp. 442-448.
Köhle et al., Gesunde Pflanzen, vol. 49, 1997, pp. 267-271.
Proc. Brighton Crop Protection Conference- Pests and Diseases, 5-3, 1992, p. 411.
Proc. Brighton Crop Protection Conference- Pests and Diseases, 5-4, 1992, p. 419.

* cited by examiner

METHOD FOR YIELD IMPROVEMENT IN GLYPHOSATE-RESISTENT LEGUMES

The present invention relates to a method for increasing the yield in glyphosate-resistant legumes, which comprises treating the plants or the seed with a mixture comprising a) a compound of the formula I

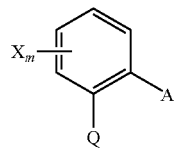

in which
X is halogen, $C_1$-$C_4$-alkyl or trifluoromethyl,
m is 0 or 1,
Q is C(=CH—$CH_3$)—$COOCH_3$, C(=CH—$OCH_3$)—$COOCH_3$, C(=N—$OCH_3$)—$CONHCH_3$, C(=N—$OCH_3$)—$COOCH_3$ or N(—$OCH_3$)—$COOCH_3$,
A is —O—B, —$CH_2$O—B, —$OCH_2$—B, —CH=CH—B, —C≡C—B, —$CH_2$O—N=C($R^1$)—B or —$CH_2$O—N=C($R^1$)—C($R^2$)=N—$OR^3$, where
B is phenyl, naphthyl, 5-membered or 6-membered hetaryl or 5-membered or 6-membered heterocyclyl, comprising one to three N atoms and/or one O or S atom or one or two O and/or S atoms, the ring systems being unsubstituted or substituted by one to three radicals $R^a$:

$R^a$ being cyano, nitro, amino, aminocarbonyl, aminothiocarbonyl, halogen, $C_1$-$C_6$-alkyl, $C_1$-$C_6$-haloalkyl, $C_1$-$C_6$-alkylcarbonyl, $C_1$-$C_6$-alkylsulfonyl, $C_1$-$C_6$-alkylsulfoxyl, $C_3$-$C_6$-cycloalkyl, $C_1$-$C_6$-alkoxy, $C_1$-$C_6$-haloalkoxy, $C_1$-$C_6$-alkyloxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, phenyl, phenoxy, benzyl, benzyloxy, 5- or 6-membered heterocyclyl, 5- or 6-membered hetaryl, 5- or 6-membered hetaryloxy, C(=NOR')—OR" or OC(R')$_2$—C(R")=NOR"
the cyclic radicals, in turn, being unsubstituted or substituted by one to three radicals $R^b$:

$R^b$ being cyano, nitro, halogen, amino, aminocarbonyl, aminothiocarbonyl, $C_1$-$C_6$-alkyl, $C_1$-$C_6$-haloalkyl, $C_1$-$C_6$-alkylsulfonyl, $C_1$-$C_6$-alkylsulfoxyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, $C_3$-$C_6$-cycloalkyl, $C_3$-$C_6$-cycloalkenyl, phenyl, phenoxy, phenylthio, benzyl, benzyloxy, 5- or 6-membered heterocyclyl, 5- or 6-membered hetaryl, 5- or 6-membered hetaryloxy or C(=NOR')—OR",
R' is hydrogen, cyano, $C_1$-$C_6$-alkyl, $C_3$-$C_6$-cycloalkyl or $C_1$-$C_4$-haloalkyl,
R" is hydrogen, $C_1$-$C_6$-alkyl, $C_3$-$C_6$-alkenyl, $C_3$-$C_6$-alkynyl, $C_1$-$C_4$-haloalkyl, $C_3$-$C_6$-haloalkenyl or $C_3$-$C_6$-haloalkynyl,
$R^1$ is hydrogen, cyano, $C_1$-$C_4$-alkyl, $C_1$-$C_4$-haloalkyl, $C_3$-$C_6$-cycloalkyl or $C_1$-$C_4$-alkoxy, $R^2$ is phenyl, phenylcarbonyl, phenylsulfonyl, 5- or 6-membered hetaryl, 5- or 6-membered hetarylcarbonyl or 5- or 6-membered hetarylsulfonyl, the ring systems being unsubstituted or substituted by one to three radicals $R^a$,
$C_1$-$C_{10}$-alkyl, $C_3$-$C_6$-cycloalkyl, $C_2$-$C_{10}$-alkenyl, $C_2$-$C_{10}$-alkynyl, $C_1$-$C_{10}$-alkylcarbonyl, $C_2$-$C_{10}$-alkenylcarbonyl, $C_3$-$C_{10}$-alkynylcarbonyl, $C_1$-$C_{10}$-alkylsulfonyl or C(R')=NOR", the hydrocarbon radicals of these groups being unsubstituted or substituted by one to three radicals $R^c$:

$R^c$ being cyano, nitro, amino, aminocarbonyl, aminothiocarbonyl, halogen, $C_1$-$C_6$-alkyl, $C_1$-$C_6$-haloalkyl, $C_1$-$C_6$-alkylsulfonyl, $C_1$-$C_6$-alkylsulfoxyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylaminothiocarbonyl, di-$C_1$-$C_6$-alkylaminothiocarbonyl, $C_2$-$C_6$-alkenyl, $C_2$-$C_6$-alkenyloxy, $C_3$-$C_6$-cycloalkyl, $C_3$-$C_6$-cycloalkyloxy, 5- or 6-membered heterocyclyl, 5- or 6-membered heterocyclyloxy, benzyl, benzyloxy, phenyl, phenoxy, phenylthio, 5- or 6-membered hetaryl, 5- or 6-membered hetaryloxy and hetarylthio, it being possible for the cyclic groups, in turn, to be partially or fully halogenated or to have attached to them one to three radicals $R^a$, and $R^3$ is hydrogen, $C_1$-$C_6$-alkyl, $C_2$-$C_6$-alkenyl or $C_2$-$C_6$-alkynyl, the hydrocarbon radicals of these groups being unsubstituted or substituted by one to three radicals $R^c$, and b) a glyphosate derivative
in a synergistically active amount.

It is already known from the literature that active ingredients of the formula I, which are generally referred to as strobilurins, are capable of bringing about increased yields in crop plants in addition to their fungicidal action (Koehle H. et al. in *Gesunde Pflanzen* 49 (1997), pages 267-271; Glaab J. et al. *Planta* 207 (1999), 442-448).

Furthermore, it is known from WO-A 97/36488 that the application of glyphosate derivatives in glyphosate-tolerant plants selected from the group consisting of sugar beet, fodder beet, maize, oilseed rape and cotton may bring about increased yields. Furthermore, it is known from U.S. Pat. No. 3,988,142 that the sublethal application of glyphosate in plants such as sugar cane increases starch and sugar production and thus the overall yield of the plant.

Surprisingly, it has now been found that the application of glyphosate and strobilurins such as, in particular, pyraclostrobin results in a synergistic effect in legumes. This means that the purely additive (in mathematical terms) yield-increasing effect of strobilurin and of the glyphosate derivative is surpassed by application of the mixture according to the invention. This synergistic effect is more than surprising, since normally it can be assumed that a fungicide and herbicide have completely different mechanisms of action.

Accordingly, the method defined at the outset has been found. The active ingredients of the formula I which are used are known as fungicides and in some cases also as insecticides (EP-A 253 213; WO-A 95/18789; WO-A 95/24396; WO-A 96/01256; WO-A 97/15552). However, there has been no suggestion to date that these active ingredients in combination with glyphosate derivatives might possibly bring about an increased yield in legumes.

The good tolerance of the active ingredients of the formula I by plants, at the concentrations required for controlling plant diseases, permits the treatment of aerial plant parts.

In the method according to the invention, the active ingredient I is preferably taken up by the leaves and distributed throughout the entire plant in the plant sap.

In a preferred embodiment of the method, the aboveground plant parts of genetically modified legumes are treated with a mixture according to the invention comprising a) a strobilurin derivative I and b) a glyphosate derivative. The application of glyphosate reduces the competition of the crop plant and the weed plants for nutrients and light and thus increases the yield of the crop plant. The mixture according to the invention is especially preferably applied to the aboveground part of the plant.

Methods for generating plants which are resistant to the effect of glyphosate are described in the more recent literature (EP-A 218 571, EP-A 293 358, WO-A 92/00377 and WO-A 92/04449). Chemical Abstracts, 123, No. 21 (1995) A.N. 281158c describes the generation of glyphosate-resistant soybean plants. Other glyphosate-resistant legumes can be generated in a similar manner. Methods for the transformation of legumes are known in the literature and can be used— as outlined further above—for generating, for example, glyphosate-resistant beans, peas, lentils, peanuts and lupins: *Plant Science (Shannon)* 150(1) Jan. 14, 2000, 41-49; *J. of Plant Biochemistry & Biotechnology* 9(2) July, 2000, 107-110; *Acta Physiologiae Plantarum* 22(2), 2000, 111-119; *Molecular Breeding* 5(1) 1999, 43-51; *In Vitro Cellular & Developmental Biology, Animal* 34 (3 Part 2) March, 1998, 53A; *Plant Cell Reports* 16(8), 1997, 513-519 and 541-544; *Theoretical & Applied Genetics* 94(2), 1997, 151-158; *Plant Science*, 117 (1-2), 1996, 131-138; *Plant Cell Reports* 16(1-2), 1996, 32-37.

For example soya varieties such as NIDERA AX 4919® which are resistant to numerous fungal diseases and the herbicide glyphosate can be used.

The preparation of the active ingredients used in the method according to the invention is known from the literature cited at the outset.

Active ingredients with the following meanings of the substituents, in each case on their own or in combination, are especially preferred for the method according to the invention:

Especially preferred active ingredients for the method according to the invention are, in particular, those of the formulae Ia to Ig in which V is $OCH_3$ or $NHCH_3$ and Y is CH or N.

Preferred active ingredients of the formula I in which Q is $C(=N-OCH_3)-COOCH_3$ are the compounds described in the publications EP-A 253 213 and EP-A 254 426.

Preferred active ingredients of the formula I in which Q is $C(=N-OCH_3)-CONHCH_3$ are the compounds described in the publications EP-A 398 692, EP-A 477 631 and EP-A 628 540.

Preferred active ingredients of the formula I in which Q is $N(-OCH_3)-COOCH_3$ are the compounds described in the publications WO-A 93/15046 and WO-A 96/01256.

Preferred active ingredients of the formula I in which Q is $C(=CH-OCH_3)-COOCH_3$ are the compounds described in the publications EP-A 178 826 and EP-A 278 595.

Preferred active ingredients of the formula I in which Q is $C(=CH-CH_3)-COOCH_3$ are the compounds described in the publications EP-A 280 185 and EP-A 350 691.

Preferred active ingredients of the formula I in which A is $-CH_2O-N=C(R^1)-B$ are the compounds described in the publications EP-A 460 575 and EP-A 463 488.

Preferred active ingredients of the formula I in which A is $-O-B$ are the compounds described in the publications EP-A 382 375 and EP-A 398 692.

Preferred active ingredients of the formula I in which A is $-CH_2O-N=C(R^1)-C(R^2)=N-OR^3$ are the compounds described in the publications WO-A 95/18789, WO-A 95/21153, WO-A 95/21154, WO-A 97/05103, WO-A 97/06133 and WO-A 97/15552.

Especially preferred are active ingredients of the formula I in which

Q is $C(=N-OCH_3)-COOCH_3$ or $C(=N-OCH_3)-CONHCH_3$,

A is $CH_2-O-$ and

B is $-N=C(R^1)-C(R^2)=N-OR^3$, where $R^1$ is hydrogen, cyano, cyclopropyl, $C_1$-$C_4$-alkyl or $C_1$-$C_2$-haloalkyl, in particular methyl, ethyl, 1-methylethyl or trifluoromethyl, and $R^2$ is $C_1$-$C_4$-alkyl, $C_2$-$C_5$-alkenyl, phenyl which is substituted by one or two halogen atoms, or is $C(R')=NOR''$, where $R'$ is one of the groups mentioned above under $R^1$ and $R''$ is hydrogen, cyclopropyl or $C_1$-$C_4$-alkyl, in particular methyl, ethyl or isopropyl, and $R^3$ is one of the groups mentioned under $R''$;

these active ingredients are described by the formula Ib

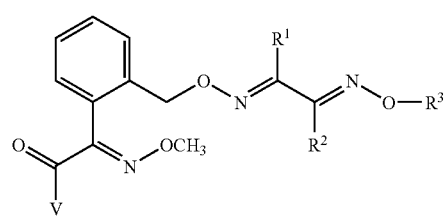

Ib in which the variables have the abovementioned meanings.

Active ingredients of the formula Ib'

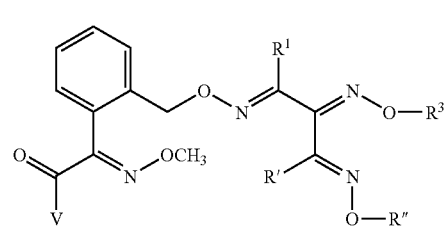

Ib' in which the variables have the abovementioned meanings are particularly preferred.

In addition, other compounds which are especially preferred are those of the formula Ia where T is CH or N and $R^a$, and $R^b$ are halogen or $C_1$-$C_4$-alkyl and x is 0, 1 or 2 and y is 0 or 1.

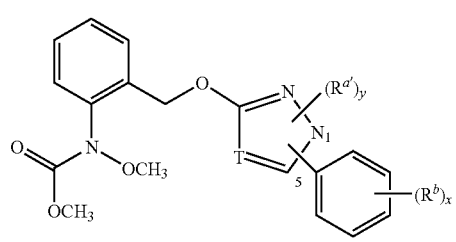

Ia

The active ingredients compiled in the tables which follow are especially preferred with regard to their use in increasing yield.

TABLE I

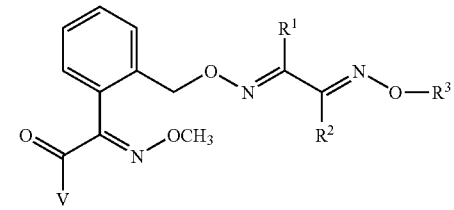

Ia

| No. | T | (Ra')y | Position of the group phenyl-(Rb)x | (Rb)x | Reference |
|---|---|---|---|---|---|
| Ia-1 | N | — | 1 | 2,4-Cl$_2$ | WO-A 96/01256 |
| Ia-2 | N | — | 1 | 4-Cl | WO-A 96/01256 |
| Ia-3 | CH | — | 1 | 2-Cl | WO-A 96/01256 |

TABLE I-continued

Ia

| No. | T | (Ra')y | Position of the group phenyl-(Rb)x | (Rb)x | Reference |
|---|---|---|---|---|---|
| Ia-4 | CH | — | 1 | 3-Cl | WO-A 96/01256 |
| Ia-5 | CH | — | 1 | 4-Cl | WO-A 96/01256 |
| Ia-6 | CH | — | 1 | 4-CH$_3$ | WO-A 96/01256 |
| Ia-7 | CH | — | 1 | H | WO-A 96/01256 |
| Ia-8 | CH | — | 1 | 3-CH$_3$ | WO-A 96/01256 |
| Ia-9 | CH | 5-CH$_3$ | 1 | 3-CF$_3$ | WO-A 96/01256 |
| Ia-10 | CH | 1-CH$_3$ | 5 | 3-CF$_3$ | WO-A 99/33812 |
| Ia-11 | CH | 1-CH$_3$ | 5 | 4-Cl | WO-A 99/33812 |
| Ia-12 | CH | 1-CH$_3$ | 5 | — | WO-A 99/33812 |

The active ingredient Ia-5 (common name: pyraclostrobin) is especially preferred.

TABLE II

II

| No. | V | R$^1$ | R$^2$ | R$^3$ | Reference |
|---|---|---|---|---|---|
| Ib-1 | OCH$_3$ | CH$_3$ | CH$_3$ | CH$_3$ | WO-A 95/18789 |
| Ib-2 | OCH$_3$ | CH$_3$ | CH(CH$_3$)$_2$ | CH$_3$ | WO-A 95/18789 |
| Ib-3 | OCH$_3$ | CH$_3$ | CH$_2$CH$_3$ | CH$_3$ | WO-A 95/18789 |
| Ib-4 | NHCH$_3$ | CH$_3$ | CH$_3$ | CH$_3$ | WO-A 95/18789 |
| Ib-5 | NHCH$_3$ | CH$_3$ | 4-F-C$_6$H$_4$ | CH$_3$ | WO-A 95/18789 |
| Ib-6 | NHCH$_3$ | CH$_3$ | 4-Cl-C$_6$H$_4$ | CH$_3$ | WO-A 95/18789 |
| Ib-7 | NHCH$_3$ | CH$_3$ | 2,4-C$_6$H$_3$ | CH$_3$ | WO-A 95/18789 |
| Ib-8 | NHCH$_3$ | Cl | 4-F-C$_6$H$_4$ | CH$_3$ | WO-A 98/38857 |
| Ib-9 | NHCH$_3$ | Cl | 4-Cl-C$_6$H$_4$ | CH$_2$CH$_3$ | WO-A 98/38857 |
| Ib-10 | NHCH$_3$ | CH$_3$ | CH$_2$C(=CH$_2$)CH$_3$ | CH$_3$ | WO-A 97/05103 |
| Ib-11 | NHCH$_3$ | CH$_3$ | CH=C(CH$_3$)$_2$ | CH$_3$ | WO-A 97/05103 |
| Ib-12 | NHCH$_3$ | CH$_3$ | CH=C(CH$_3$)$_2$ | CH$_2$CH$_3$ | WO-A 97/05103 |
| Ib-13 | NHCH$_3$ | CH$_3$ | CH=C(CH$_3$)CH$_2$CH$_3$ | CH$_3$ | WO-A 97/05103 |
| Ib-14 | NHCH$_3$ | CH$_3$ | O—CH(CH$_3$)$_2$ | CH$_3$ | WO-A 97/06133 |
| Ib-15 | NHCH$_3$ | CH$_3$ | O—CH$_2$CH(CH$_3$)$_2$ | CH$_3$ | WO-A 97/06133 |
| Ib-16 | NHCH$_3$ | CH$_3$ | C(CH$_3$)=NOCH$_3$ | CH$_3$ | WO-A 97/15552 |
| Ib-17 | NHCH$_3$ | CH$_3$ | C(CH$_3$)=NOCH$_2$CH$_3$ | CH$_2$CH$_3$ | WO-A 97/15552 |
| Ib-18 | NHCH$_3$ | CH$_3$ | C(CH$_3$)=NOCH(CH$_3$)$_2$ | CH(CH$_3$)$_2$ | WO-A 97/15552 |
| Ib-19 | NHCH$_3$ | CH$_3$ | C(CH$_3$)=NO(c-C$_3$H$_5$) | c-C$_3$H$_5$ | WO-A 97/15552 |
| Ib-20 | NHCH$_3$ | CH$_3$ | C(CH$_3$)=NOCH$_2$CH=CH$_2$ | CH$_2$CH=CH$_2$ | WO-A 97/15552 |
| Ib-21 | NHCH$_3$ | CF$_3$ | C(CF$_3$)=NOCH$_3$ | CH$_3$ | WO-A 97/15552 |
| Ib-22 | NHCH$_3$ | CF$_3$ | C(CF$_3$)=NOCH$_2$CH$_3$ | CH$_2$CH$_3$ | WO-A 97/15552 |
| Ib-23 | NHCH$_3$ | CF$_3$ | C(CF$_3$)=NOCH(CH$_3$)$_2$ | CH(CH$_3$)$_2$ | WO-A 97/15552 |
| Ib-24 | NHCH$_3$ | CF$_3$ | C(CF$_3$)=NO(c-C$_3$H$_5$) | c-C$_3$H$_5$ | WO-A 97/15552 |
| Ib-25 | NHCH$_3$ | CF$_3$ | C(CF$_3$)=NOCH$_2$CH=CH$_2$ | CH$_2$CH=CH$_2$ | WO-A 97/15552 |
| Ib-26 | OCH$_3$ | CH$_3$ | C(CH$_3$)=NOCH$_3$ | CH$_3$ | WO-A 97/15552 |
| Ib-27 | OCH$_3$ | CH$_3$ | C(CH$_3$)=NOCH$_2$CH$_3$ | CH$_2$CH$_3$ | WO-A 97/15552 |
| Ib-28 | OCH$_3$ | CH$_3$ | C(CH$_3$)=NOCH(CH$_3$)$_2$ | CH(CH$_3$)$_2$ | WO-A 97/15552 |

TABLE II-continued

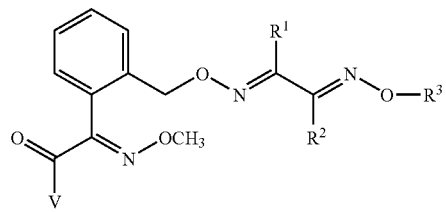

| No. | V | R¹ | R² | R³ | Reference |
|---|---|---|---|---|---|
| Ib-29 | $OCH_3$ | $CH_3$ | $C(CH_3)=NO(c-C_3H_5)$ | $c-C_3H_5$ | WO-A 97/15552 |
| Ib-30 | $OCH_3$ | $CH_3$ | $C(CH_3)=NOCH_2CH=CH_2$ | $CH_2CH=CH_2$ | WO-A 97/15552 |
| Ib-31 | $OCH_3$ | $CF_3$ | $C(CF_3)=NOCH_3$ | $CH_3$ | WO-A 97/15552 |
| Ib-32 | $OCH_3$ | $CF_3$ | $C(CF_3)=NOCH_2CH_3$ | $CH_2CH_3$ | WO-A 97/15552 |
| Ib-33 | $OCH_3$ | $CF_3$ | $C(CF_3)=NOCH(CH_3)_2$ | $CH(CH_3)_2$ | WO-A 97/15552 |
| Ib-34 | $OCH_3$ | $CF_3$ | $C(CF_3)=NO(c-C_3H_5)$ | $c-C_3H_5$ | WO-A 97/15552 |
| Ib-35 | $OCH_3$ | $CF_3$ | $C(CF_3)=NOCH_2CH=CH_2$ | $CH_2CH=CH_2$ | WO-A 97/15552 |

TABLE III

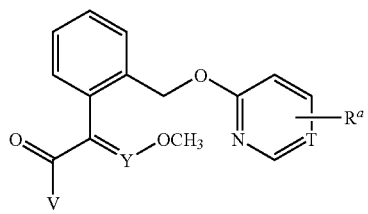

| No. | V | Y | T | $R^a$ | Reference |
|---|---|---|---|---|---|
| Ic-1 | $OCH_3$ | CH | N | 2-$OCH_3$, 6-$CF_3$ | WO-A 96/16047 |
| Ic-2 | $OCH_3$ | CH | N | 2-$OCH(CH_3)_2$, 6-$CF_3$ | WO-A 96/16047 |
| Ic-3 | $OCH_3$ | CH | CH | 5-$CF_3$ | EP-A 278 595 |
| Ic-4 | $OCH_3$ | CH | CH | 6-$CF_3$ | EP-A 278 595 |
| Ic-5 | $NHCH_3$ | N | CH | 3-Cl | EP-A 398 692 |
| Ic-6 | $NHCH_3$ | N | CH | 3-$CF_3$ | EP-A 398 692 |
| Ic-7 | $NHCH_3$ | N | CH | 3-$CF_3$, 5-Cl | EP-A 398 692 |
| Ic-8 | $NHCH_3$ | N | CH | 3-Cl, 5-$CF_3$ | EP-A 398 692 |

TABLE IV

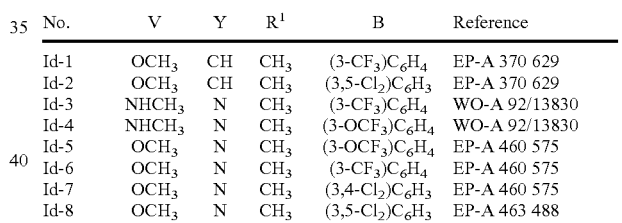

| No. | V | Y | R¹ | B | Reference |
|---|---|---|---|---|---|
| Id-1 | $OCH_3$ | CH | $CH_3$ | $(3-CF_3)C_6H_4$ | EP-A 370 629 |
| Id-2 | $OCH_3$ | CH | $CH_3$ | $(3,5-Cl_2)C_6H_3$ | EP-A 370 629 |
| Id-3 | $NHCH_3$ | N | $CH_3$ | $(3-CF_3)C_6H_4$ | WO-A 92/13830 |
| Id-4 | $NHCH_3$ | N | $CH_3$ | $(3-OCF_3)C_6H_4$ | WO-A 92/13830 |
| Id-5 | $OCH_3$ | N | $CH_3$ | $(3-OCF_3)C_6H_4$ | EP-A 460 575 |
| Id-6 | $OCH_3$ | N | $CH_3$ | $(3-CF_3)C_6H_4$ | EP-A 460 575 |
| Id-7 | $OCH_3$ | N | $CH_3$ | $(3,4-Cl_2)C_6H_3$ | EP-A 460 575 |
| Id-8 | $OCH_3$ | N | $CH_3$ | $(3,5-Cl_2)C_6H_3$ | EP-A 463 488 |

TABLE V

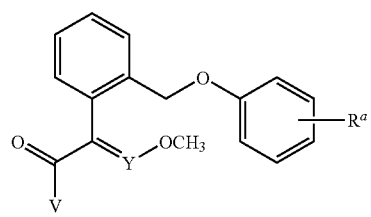

| No. | V | Y | $R^a$ | Reference |
|---|---|---|---|---|
| Ie-1 | $OCH_3$ | N | 2-$CH_3$ | EP-A 253 213 |
| Ie-2 | $OCH_3$ | N | 2,5-$(CH_3)_2$ | EP-A 253 213 |
| Ie-3 | $NHCH_3$ | N | 2,5-$(CH_3)_2$ | EP-A 477 631 |
| Ie-4 | $NHCH_3$ | N | 2-Cl | EP-A 477 631 |
| Ie-5 | $NHCH_3$ | N | 2-$CH_3$ | EP-A 477 631 |
| Ie-6 | $NHCH_3$ | N | 2-$CH_3$, 4-$OCF_3$ | EP-A 628 540 |
| Ie-7 | $NHCH_3$ | N | 2-Cl, 4-$OCF_3$ | EP-A 628 540 |

TABLE V-continued

Ie

| No. | V | Y | R$^a$ | Reference |
|---|---|---|---|---|
| Ie-8 | NHCH$_3$ | N | 2-CH$_3$, 4-OCH(CH$_3$)-C(CH$_3$)=NOCH$_3$ | EP-A 11 18 609 |
| Ie-9 | NHCH$_3$ | N | 2-Cl, 4-OCH(CH$_3$)-C(CH$_3$)=NOCH$_3$ | EP-A 11 18 609 |
| Ie-10 | NHCH$_3$ | N | 2-CH$_3$,4-OCH(CH$_3$)-C(CH$_2$CH$_3$)=NOCH$_3$ | EP-A 11 18 609 |
| Ie-11 | NHCH$_3$ | N | 2-Cl,4-OCH(CH$_3$)-C(CH$_3$)=NOCH$_2$CH$_3$ | EP-A 11 18 609 |

TABLE VI

If

| No. | V | Y | R$^a$ | Reference |
|---|---|---|---|---|
| If-1 | NHCH$_3$ | N | H | EP-A 398 692 |
| If-2 | NHCH$_3$ | N | 3-CH$_3$ | EP-A 398 692 |
| If-3 | NHCH$_3$ | N | 2-NO$_2$ | EP-A 398 692 |
| If-4 | NHCH$_3$ | N | 4-NO$_2$ | EP-A 398 692 |
| If-5 | NHCH$_3$ | N | 4-Cl | EP-A 398 692 |
| If-6 | NHCH$_3$ | N | 4-Br | EP-A 398 692 |

Fungicidal active ingredients which can be employed are the strobilurins I alone or in mixture with other fungicidal active ingredients, in particular those from the class of the azoles I$_x$.

Azole active ingredients which are suitable for this purpose are:

fluquinconazole, Proc. Br. Crop Prot. Conf.-Pests Dis., 5-3, 411 (1992);

metconazole, Proc. Br. Crop Prot. Conf.-Pests Dis., 5-4, 419 (1992);

prochloraz, U.S. Pat. No. 3,991,071;

propiconazole, GB-A 1,522,657;

prothioconazole, WO-A 96/016048;

tebuconazole, U.S. Pat. No. 4,723,984;

epoxiconazole, EP-A 196038;

myclobutanil, CAS RN [88671-89-0];

Azoles which are especially suitable are: metconazole, myclobutanil, epoxiconazole, propiconazole, prothioconazole or tebuconazole.

TABLE VII

Ig

| No. | V | Y | T | R$^a$ | Reference |
|---|---|---|---|---|---|
| Ig-1 | OCH$_3$ | CH | N | 6-O-(2-CN-C$_6$H$_4$) | EP-A 382 375 |
| Ig-2 | OCH$_3$ | CH | N | 6-O-(2-Cl-C$_6$H$_4$) | EP-A 382 375 |
| Ig-3 | OCH$_3$ | CH | N | 6-O-(2-CH$_3$-C$_6$H$_4$) | EP-A 382 375 |
| Ig-4 | NHCH$_3$ | N | N | 6-O-(2-Cl-C$_6$H$_4$) | GB-A 22 53 624 |
| Ig-5 | NHCH$_3$ | N | N | 6-O-(2,4-Cl$_2$-C$_6$H$_3$) | GB-A 22 53 624 |
| Ig-6 | NHCH$_3$ | N | N | 6-O-(2-CH$_3$-C$_6$H$_4$) | GB-A 22 53 624 |
| Ig-7 | NHCH$_3$ | N | N | 6-O-(2-CH$_3$,3-Cl-C$_6$H$_3$) | GB-A 22 53 624 |
| Ig-8 | NHCH$_3$ | N | N | 2-F, 6-O-(2-CH$_3$-C$_6$H$_4$) | WO-A 98/21189 |
| Ig-9 | NHCH$_3$ | N | N | 2-F, 6-O-(2-Cl-C$_6$H$_4$) | WO-A 98/21189 |
| Ig-10 | NHCH$_3$ | N | N | 2-F, 6-O-(2-CH$_3$,3-Cl-C$_6$H$_3$) | WO-A 98/21189 |

If fungicide mixtures of, for example, strobilurins I and azoles $I_x$ are employed, they are generally employed in a weight ratio I to $I_x$ of 20:1 to 0.05:1, preferably 10:1 to 0.1:1.

Glyphosate derivatives II are essentially understood as meaning the following compounds, which are mentioned in The Pesticide Manual: for example, glyphosate may be employed as the free acid or in the form of salts such as the isopropylammonium salt, the sodium salt, the ammonium salt or the trimesium (trimethylsulfenium) salt. Mixtures of the salts may also be employed. Moreover, the glyphosate derivatives II include the compound N-(phosphonomethyl)glycine. The preparation of the glyphosate derivatives II can be found in the literature cited in The Pesticide Manual (12th edition).

The compounds I in combination with glyphosate derivatives raise the yield potential in legumes. They are especially important for the treatment of various glyphosate-resistant crop plants such as peas, beans, lentils, peanuts, lupins and in particular soybeans. The synergistic effect is demonstrated independently of the generation of the glyphosate-resistant legumes.

Specifically, they are suitable for controlling the following symptoms:
 signs of wilting despite the availability of sufficient nutrients,
 discolorations of the green leaf tissue such as, for example bleaching of soybeans.

The compounds I are applied by treating the plants to be protected with an effective amount of the active ingredients. Application can be effected both before and after application of the glyphosate derivatives II to the plants.

In a preferred embodiment of the method, the treatment of the plant is effected jointly with the application of the fungicide I and the herbicide II. The synergistic effect is particularly pronounced in this case.

When using an active ingredient I, the application rates are in the range of from 0.01 to 2.0 kg of active ingredient per hectare, depending on the weather conditions and the plant species.

When using a glyphosate derivative II, the application rates are in the range of from 0.1 to 6.0 kg of active ingredient (acid equivalent) per hectare, depending on the weather conditions and the plant species.

As a rule, the fungicide I, or the fungicidal mixture I and $I_x$, is employed in a weight ratio to the herbicide II of 5:1 to 0.01:1, preferably 1:1 to 0.1:1.

The compounds I and the glyphosate derivatives II may be converted into the formulations conventionally used for crop protection products, for example solutions, emulsions, suspensions, dusts, powders, pastes and granules. The use form depends on the application in question; in any case, it should ensure uniform and even distribution of the mixture according to the invention.

The formulations are prepared in the known manner, for example by extending the active ingredient with solvents and/or carriers, if desired using emulsifiers and dispersants, it also being possible to use other organic solvents as cosolvents if water is used as the diluent. Auxiliaries are essentially those also conventionally used for fungicides.

In general, the formulations comprise between 0.01 and 95% by weight, preferably between 0.1 and 90% by weight, of the active ingredient. The active ingredients are employed in a purity of from 90% to 100%, preferably 95% to 100% (according to NMR spectrum).

Examples of formulations are known from the publications cited at the outset.

Aqueous use forms can usually be prepared from emulsion concentrates, pastes or wettable powders (sprayable powders, oil dispersions) by addition of water. To prepare emulsions, pastes or oil dispersions, the substances, as such or dissolved in an oil or solvent, may be homogenized in water by means of wetter, sticker, dispersant or emulsifier. Alternatively, it is possible to prepare concentrates consisting of active substance, wetter, sticker, dispersant or emulsifier and, if appropriate, solvent or oil, and such concentrates are suitable for dilution with water.

The active ingredient concentrations in the ready-to-use products may be varied within substantial ranges. In general, they are between 0.0001 and 10%, preferably between 0.01 and 1%.

The active ingredients may also be used successfully by the ultra-low-volume (ULV) method, it being possible to apply formulations comprising more than 95% by weight of active ingredient, or indeed the active ingredient without additions.

Various types of oils or herbicides, other fungicides, other pesticides or bactericides may be added to the active ingredients, if appropriate just prior to use (tank mix). These agents can be admixed with the compositions according to the invention in a weight ratio of from 1:10 to 10:1.

The active ingredients I are preferably applied to the plant jointly or separately with the glyphosate II.

In general, the compounds I and II are applied within a period of 3 weeks to 3 months, preferably within 1 to 2 months, after planting the legume seeds. It may be advantageous to carry out the fungicide or herbicide treatment repeatedly, preferably twice.

In the case of separate use, it may be advantageous to apply the herbicide II for example 3-6 weeks after planting the legume seeds and then to apply either the fungicide I alone or a mixture of fungicide I and herbicide II in a second application 4-8 weeks after planting.

In the case of joint application, a mixture of the compounds I and II is generally applied once to twice within a period of 1 to 3 months after planting the legume seeds.

The abovementioned application methods are understood as meaning foliar treatment of the legumes. In comparison to, for example, a seed treatment, these methods have pronounced advantages.

The use examples demonstrate the increased yield achieved by the use of pyraclostrobin and glyphosate in soya plantations.

It must be added that the increased yield is not connected to a successful control of harmful fungi. In the experiments, the experimental fields were free from disease. Naturally, in such a case the yield would be increased even more since the fungicidal active ingredients I (strobilurins) and $I_x$ (azoles) or their mixtures constitute extremely efficient fungicides. Yield losses caused by harmful fungi can be counteracted effectively by the methods according to the invention.

Mention of the use according to the invention of the active ingredients I may be made in the form of an imprint on the packaging or else in product data sheets. Such mention may also be made in the case of products which can be used in combination with the active ingredients I.

Use examples for the increased yield in legumes

USE EXAMPLE

The results shown hereinbelow were obtained in experiments in the, open which were carried out during the winter season in the Argentinian northern pampas. The plots used were arranged randomly relative to one another. Each treatment variant was replicated-four times. The crop plant used was the soya variety NIDERA AX 4910, which is resistant to numerous fungal diseases and to the herbicide glyphosate.

In all 5 experiments, two foliar treatments with glyphosate were carried out 30 or 60 days after planting the soya seeds, using equipment conventionally used under practice conditions. In the experiments 2 and 3, pyraclostrobin was added at "30 days after planting", while pyraclostrobin was added at "60 days after planting" in the experiments 4 and 5. As demonstrated by the results, the addition of pyraclostrobin in amounts of 50 or 100 g of a.s./ha at both the early and the late treatment times markedly increased the yield in comparison with the conventional use of glyphosate alone.

| Experiment number | Treatment 30 days after planting | a.s. g/ha | Treatment 60 days after planting | a.s. g/ha | Yield |
|---|---|---|---|---|---|
| 1 | glyphosate | 360 | glyphosate | 360 | 100% |
| 2 | glyphosate pyraclostrobin | 360 50 | glyphosate | 360 | 116% |
| 3 | glyphosate pyraclostrobin | 360 100 | glyphosate | 360 | 129% |
| 4 | glyphosate | 360 | glyphosate pyraclostrobin | 360 50 | 122% |
| 5 | glyphosate | 360 | glyphosate pyraclostrobin | 360 100 | 135% | a.s. = active substance

We claim:

1. A method for synergistically increasing the yield in glyphosate-resistant legumes, which comprises treating the plants with a mixture comprising
   (a) a compound of the formula Ia

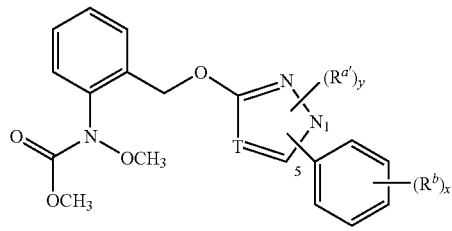

Ia in which
   T is CH or N;
   $R^{a१}$ and $R^b$ are halogen or $C_1$-$C_4$-alkyl;
   the phenyl group is in the 1- or 5-position;
   x is 0, 1 or 2; and
   y is 0 or 1; and
   (b) a glyphosate derivative II selected from the group consisting of N-(phosphonomethyl)glycine as a free acid or a salt thereof in a synergistically active amount, wherein the weight ratio of the compound of the formula Ia to the glyphosate derivative II is from 1:1 to 0.01:1.

2. The method as claimed in claim 1, wherein the salt of N-(phosphonomethyl)glycine is selected from the group consisting of the isopropylammonium salt, sodium salt, ammonium salt and trimethylsulfenium salt.

3. The method as claimed in claim 1, wherein the mixture comprises:
   (a) pyraclostrobin and
   (b) a glyphosate derivative II.

4. The method as claimed in claim 1, wherein component (b) is N-(phosphonomethyl)glycine as a free acid.

5. A method as claimed in claim 1, wherein a fungicidal azole selected from the group consisting of: fluquinconazole, metconazole, prochloraz, propiconazole, prothioconazole, tebuconazole, epoxiconazole or myclobutanil is employed as component a) in addition to the active compound of the formula Ia.

6. A synergistic mixture comprising
   (a) a compound of the formula Ia

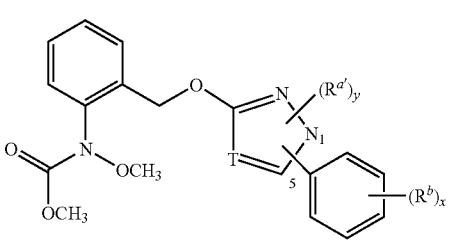

Ia in which
   T is CH or N;
   $R^{a१}$ and $R^b$ are halogen or $C_1$-$C_4$-alkyl;
   the phenyl group is in the 1- or 5-position;
   x is 0, 1 or 2; and
   y is 0 or 1; and
   (b) a glyphosate derivative II selected from the group consisting of N-(phosphonomethyl)glycine as a free acid or a salt thereof
   wherein the weight ratio of the compound of the formula Ia to the glyphosate derivative II is from 1:1 to 0.01:1.

7. A synergistic mixture as claimed in claim 6, wherein the mixture comprises:
   (a) pyraclostrobin and
   (b) a glyphosate derivative II.

8. A synergistic mixture as claimed in claim 7, wherein component a) comprises an azole selected from the group consisting of: metconazole, myclobutanil, epoxiconazole, propiconazole, prothioconazole and tebuconazole in addition to the active compound pyraclostrobin.

9. A synergistic mixture as claimed in claim 7, wherein component (b) is a salt of N-(phosphonomethyl)glycine selected from the group consisting of the isopropylammonium salt, sodium salt, ammonium salt and trimethylsulfenium salt.

10. The method as claimed in claim 3, wherein the weight ratio of the compound pyraclostrobin to the glyphosate derivative II is 1:1 to 0.1:1.

11. A synergistic mixture as claimed in claim 7, wherein the weight ratio of the compound pyraclostrobin to the glyphosate derivative II is 1:1 to 0.1:1.

* * * * *